(12) United States Patent
Meridew et al.

(10) Patent No.: US 8,585,770 B2
(45) Date of Patent: Nov. 19, 2013

(54) IMPLANT SLEEVE FOR CEMENT HIP STEMS

(75) Inventors: Jason D. Meridew, Warsaw, IN (US); John R. White, Winona Lake, IN (US); Mark A. Bollinger, Fort Wayne, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 168 days.

(21) Appl. No.: 13/181,091

(22) Filed: Jul. 12, 2011

(65) Prior Publication Data
US 2013/0018482 A1     Jan. 17, 2013

(51) Int. Cl.
*A61F 2/30*        (2006.01)
(52) U.S. Cl.
USPC ............... 623/23.46; 623/23.44; 623/22.11
(58) Field of Classification Search
CPC ....................................................... A61F 2/36
USPC ................................ 623/22.11, 23.44–23.46
See application file for complete search history.

(56) References Cited

U.S. PATENT DOCUMENTS

| | | | |
|---|---|---|---|
| 3,605,123 A | 9/1971 | Hahn | |
| 3,906,550 A | 9/1975 | Rostoker et al. | |
| 4,064,567 A | 12/1977 | Burstein et al. | |
| 4,065,817 A * | 1/1978 | Branemark et al. | 623/23.46 |
| 4,608,052 A | 8/1986 | Van Kampen et al. | |
| 5,035,713 A | 7/1991 | Friis | |
| 5,035,714 A * | 7/1991 | Willert et al. | 623/23.62 |
| 5,108,432 A | 4/1992 | Gustavson | |
| 5,108,435 A | 4/1992 | Gustavson et al. | |
| 5,133,767 A | 7/1992 | Frey et al. | |
| 5,258,034 A | 11/1993 | Furlong et al. | |
| 5,376,123 A | 12/1994 | Klaue et al. | |
| 5,672,284 A | 9/1997 | Devanathan et al. | |
| 5,885,295 A | 3/1999 | McDaniel et al. | |
| 5,984,968 A | 11/1999 | Park | |
| 6,312,473 B1 | 11/2001 | Oshida | |
| 2009/0076508 A1 | 3/2009 | Weinans et al. | |
| 2009/0204226 A1 | 8/2009 | Fonte | |

OTHER PUBLICATIONS http://www.alphatecspine.com/products/osseofix.asp, "OsseoFix® Spinal Fracture Reduction System", 1 page, 2008.

* cited by examiner

*Primary Examiner* — Jason-Dennis Stewart
(74) *Attorney, Agent, or Firm* — Harness, Dickey

(57) ABSTRACT

An implant sleeve operable to center an implant at an implantation site. The implant sleeve includes a proximal end, a distal end, an annular sidewall, a mesh portion of the annular sidewall, and an interior area. The annular sidewall is between the proximal end and the distal end. The mesh portion defines a plurality of openings in the annular sidewall. The interior area is defined by the annular sidewall and is configured to receive a stem of the implant. A longitudinal axis of the implant sleeve extends along an axial center of the interior area. In response to force applied to the implant sleeve, the implant sleeve compresses and the mesh portion expands outward from the longitudinal axis.

20 Claims, 10 Drawing Sheets

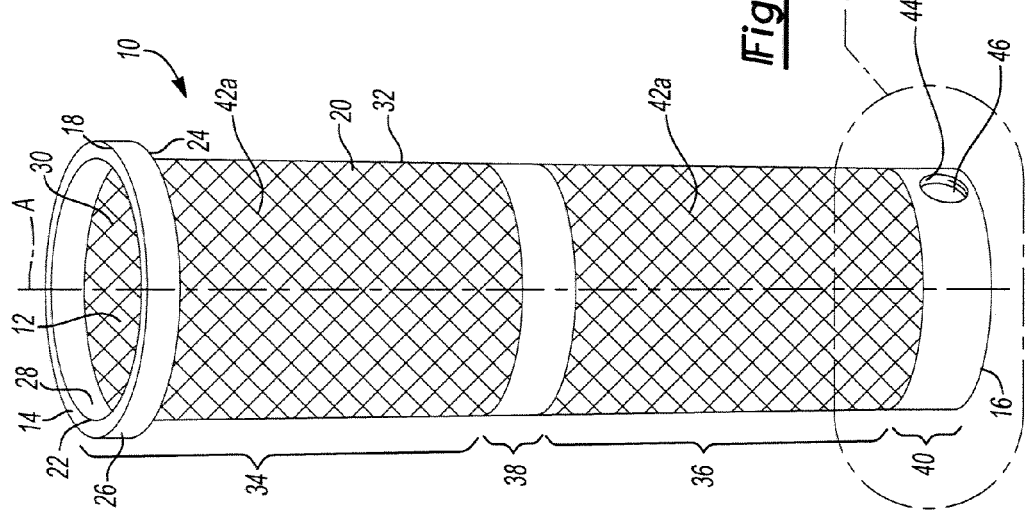
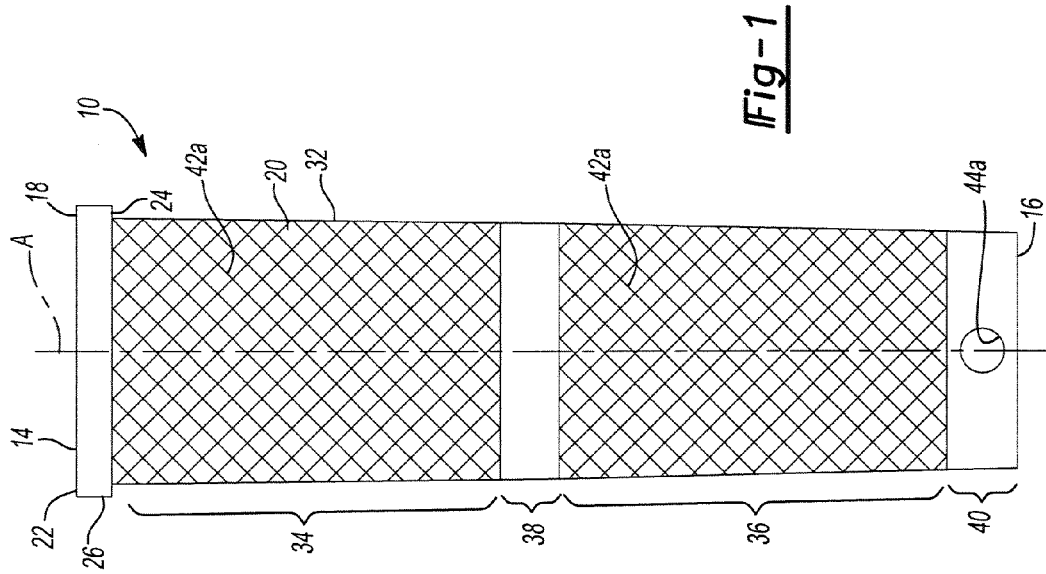

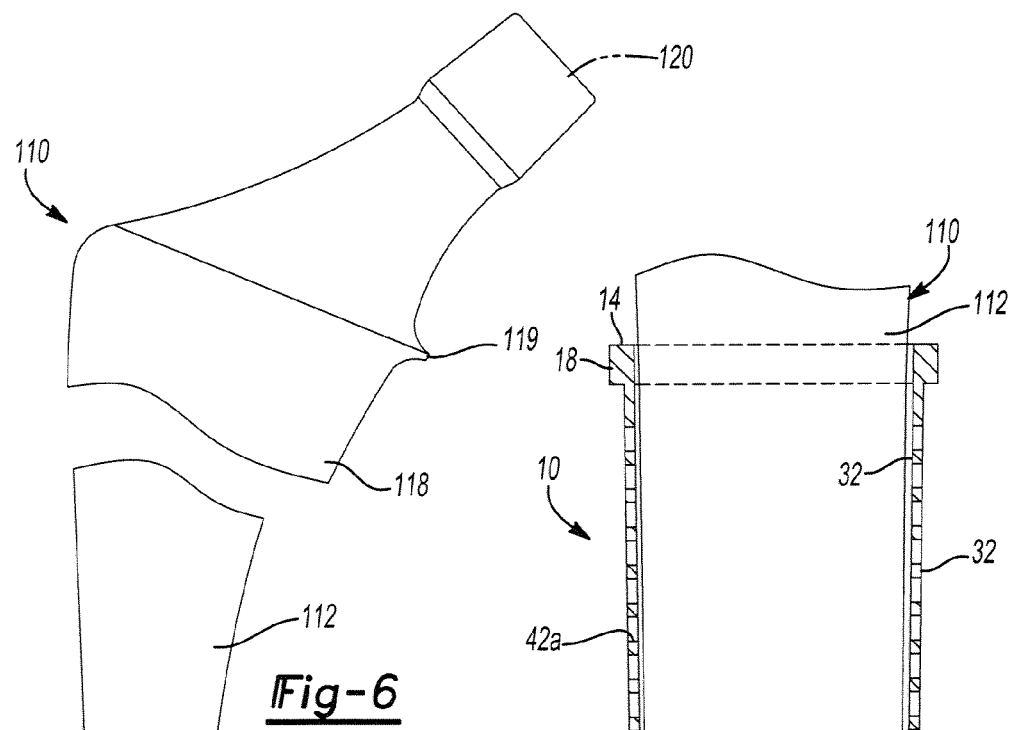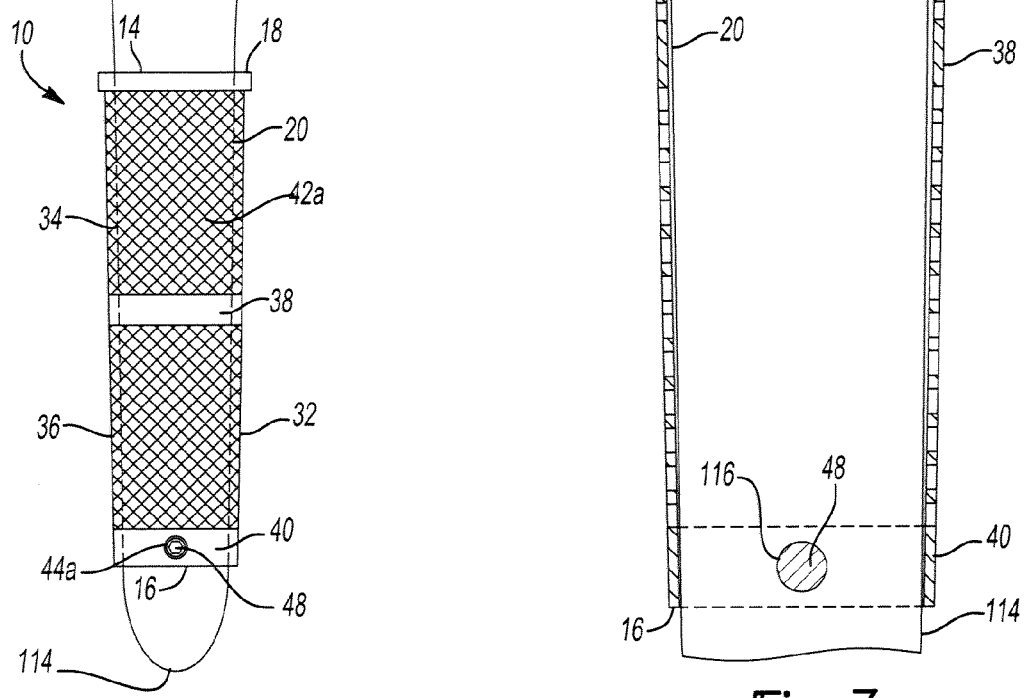

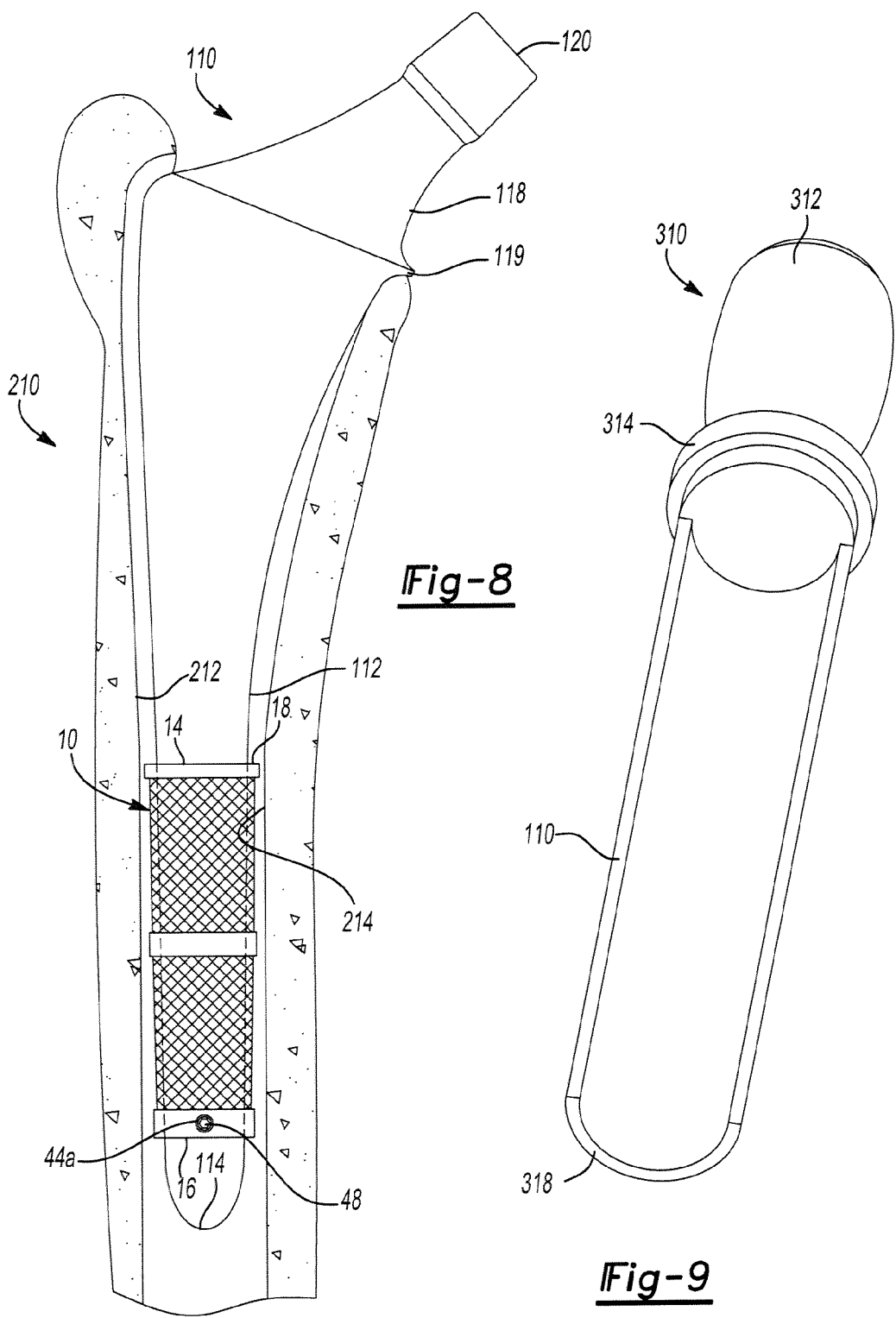

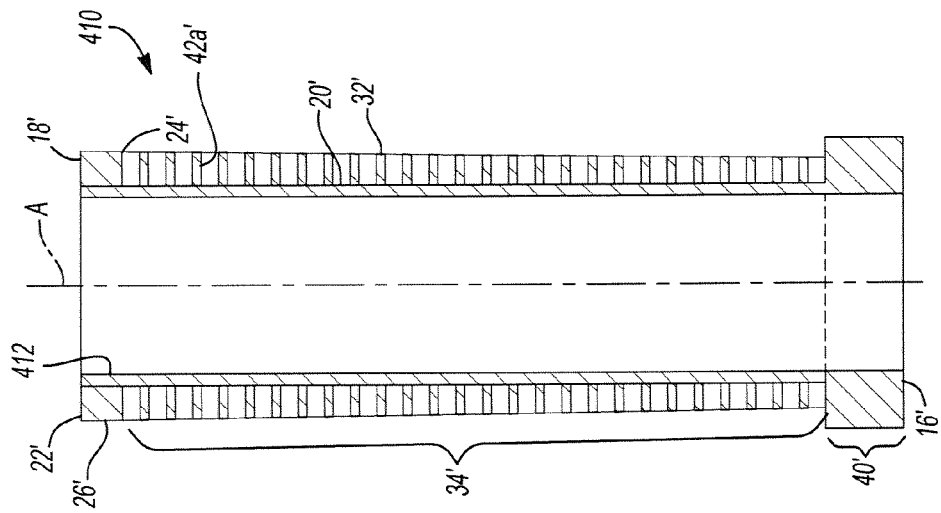
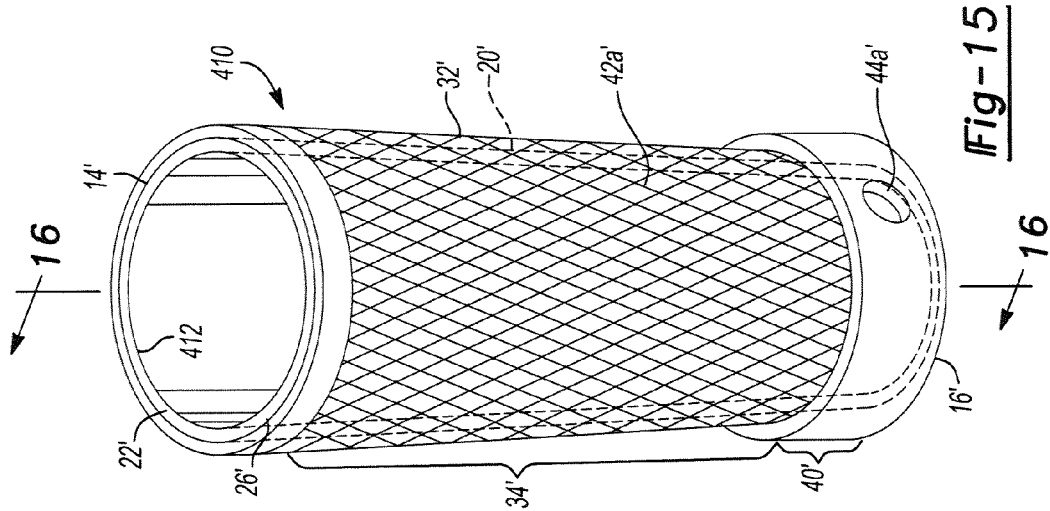

IMPLANT SLEEVE FOR CEMENT HIP STEMS

FIELD

The present disclosure relates to implant sleeves for positioning orthopedic implants at an implant site.

BACKGROUND

This section provides background information related to the present disclosure which is not necessarily prior art.

During implantation of an implant, it is often desirable to center the implant at an implantation site. For example, it is often desirable to center a hip stem in an intramedullary canal of a femur prior to fixation, such as with bone cement. While current centering devices and methods are suitable, they are subject to improvement.

SUMMARY

This section provides a general summary of the disclosure, and is not a comprehensive disclosure of its full scope or all of its features.

The present teachings provide for an implant sleeve operable to center an implant at an implantation site. The implant sleeve includes a first end, a second end, a shaped outer sidewall, a mesh portion of the sidewall, and an interior area. The outer sidewall is between the first end and the second end. The mesh portion defines a plurality of openings in the outer sidewall. The interior area is encompassed by the sidewall and is configured to receive a stem of the implant. A longitudinal axis of the implant sleeve extends along an axial center of the interior area. In response to force applied to the implant sleeve, the implant sleeve compresses and the mesh portion expands outward from the longitudinal axis.

The present teachings further provide for an implant sleeve operable to center an implant at an implantation site. The implant sleeve includes a rigid first end portion at a first end of the implant sleeve, an annular sidewall extending from the rigid first end portion to a second end of the implant sleeve, and a rigid second end portion at the second end of the implant sleeve. The annular sidewall defines an interior area of the implant sleeve that is configured to receive a stem of the implant. An aperture is defined by one of the rigid first end portion and the rigid second end portion. The aperture is configured to receive a fastener there through to secure the implant sleeve to the stem. A mesh portion forms a portion of the annular sidewall between the rigid first end portion and the rigid second end portion, the mesh portion expands outward from a longitudinal axis of the interior area in response to a compression force applied to one of the rigid first end portion or the rigid second end portion.

The present teachings further provide for a method for centering a stem of an implant at an implantation site. The method includes the following: implanting at the implantation site the implant having a sleeve rigidly mounted to the stem of the implant, the stem extends through an interior area of the sleeve; and compressing the sleeve by applying force to the sleeve to expand a mesh portion of the sleeve outward from the stem and into engagement with sidewalls of the implantation site to thereby center the stem at the implantation site.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a side view of an implant sleeve according to the present teachings;

FIG. 2 is a perspective view of the implant sleeve of FIG. 1;

FIG. 6 is a side view of the implant sleeve of FIG. 1 mounted on a femoral implant;

FIG. 7 is a cross-sectional view of the implant sleeve of FIG. 1 mounted on the femoral implant;

FIG. 8 is a cross-sectional view of a femur, the femoral implant with the implant sleeve mounted thereto is seated in an intramedullary canal of the femur;

FIG. 9 is a perspective view of a compression tool;

FIG. 15 is a perspective view of another implant sleeve according to the present teachings;

FIG. 16 is a cross-sectional view taken along line 16-16 of FIG. 15; and

Corresponding reference numerals indicate corresponding parts throughout the several views of the drawings.

DETAILED DESCRIPTION

Exemplary embodiments will now be described more fully with reference to the accompanying drawings.

Figure 3:
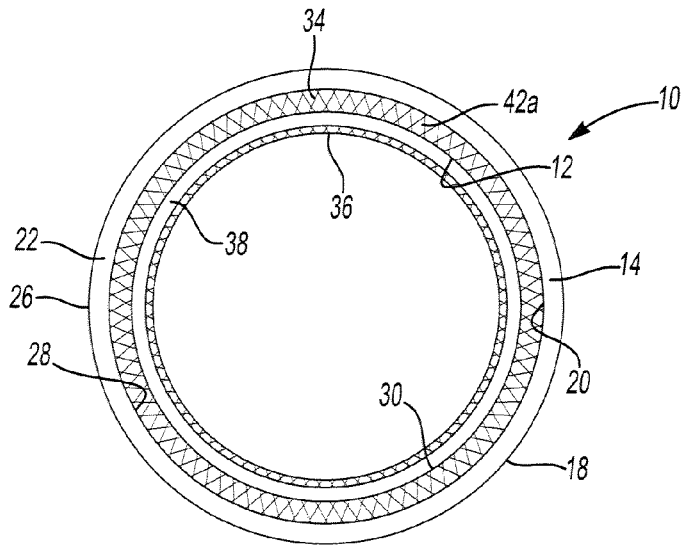
FIG. 3 is a top view of the implant sleeve of FIG. 1.

With initial reference to FIGS. 1-3, an implant sleeve according to the present teachings is illustrated at reference numeral 10. The implant sleeve 10 is generally tube-shaped, and thus defines an interior area 12 (FIGS. 2 and 3). The implant sleeve 10 includes a first end 14 and a second end 16. For example and as described herein, the first end 14 can be a proximal end and the second end 16 can be a distal end. At the proximal end 14 is an annular flange 18. An annular sidewall 20 extends from the annular flange 18 to the distal end 16. A longitudinal axis A of the implant sleeve 10 extends along an axial center of the interior area 12 between the proximal end 14 and the distal end 16. Although the sleeve 10 is illustrated and discussed to generally include an annular tube shape, the sleeve 10 may include or define any appropriate shape. The implant sleeve 10 can be made of any suitable biocompatible metal, such as cobalt chrome, titanium, steel, or shape memory alloys (such as Nitinol™). The implant sleeve 10 can also be made of a suitable non-metal, such as polyether ether ketone (PEEK), polyethylene, or a suitable resorbable polymer, The annular flange 18 generally includes a proximal flange surface 22, a distal flange surface 24 that is opposite to the proximal flange surface 22, an outer flange surface 26, and an inner flange surface 28 that is opposite to the outer flange surface 26. The annular flange 18 is rigid and cannot be compressed or expanded by force typically applied by hand or with instruments in the operating room. The inner flange surface 28 defines the interior area 12 at the proximal end 14. The annular flange 18 has a greater outer diameter than an outer diameter of the annular sidewall 20. As a result, the annular flange 18 extends a greater distance outward from the longitudinal axis A than the annular sidewall 20 does. The distal flange surface 24 thus overhangs the annular sidewall 20, as illustrated in FIG. 1 for example. The annular flange 18 can alternatively be flush with the annular sidewall 20 so that it does not extend beyond the annular sidewall 20.

The annular sidewall 20 includes an inner sidewall surface 30 and an outer sidewall surface 32 that is opposite to the inner sidewall surface 30. The inner sidewall surface 30 defines the interior area 12 from the annular flange 18 to the distal end 16 to be generally cylindrical. The annular sidewall 20 can be tapered from the annular flange 18 at the proximal end 14 to the distal end 16, as illustrated. Thus, the taper of the interior area 12 can correspond to a taper of an implant stem. The annular sidewall 20 and interior area 12 can be linear (not tapered) to accommodate a linear implant stem.

The annular sidewall 20 further includes a first mesh portion 34, a second mesh portion 36, an intermediate sidewall portion 38, and a distal sidewall portion 40. The distal sidewall portion 40 is at the distal end 16. The intermediate sidewall portion 38 is generally midway between the annular flange 18 and the distal sidewall portion 40 of the annular sidewall 20. The first mesh portion 34 is between the annular flange 18 and the intermediate sidewall portion 38. The second mesh portion 36 is between the intermediate sidewall portion 38 and the distal sidewall portion 40.

Figure 4:
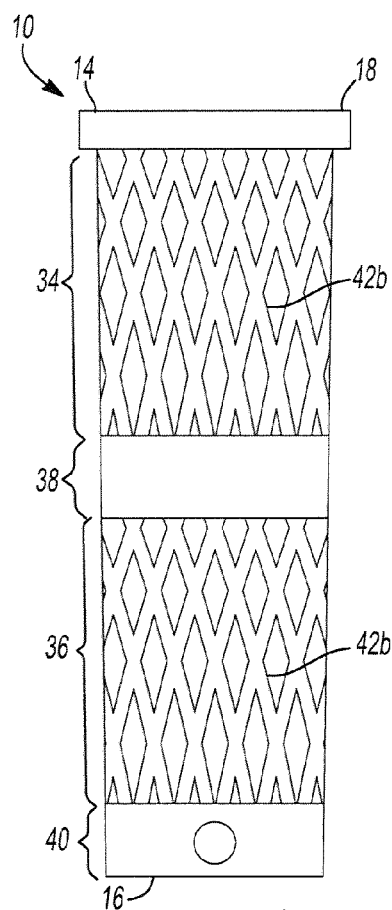
FIG. 4 is a side view of an additional implant sleeve according to the present teachings.

At the first mesh portion 34 and the second mesh portion 36, the annular sidewall 20 defines a plurality of openings 42a that extend completely through the annular sidewall 20 between the outer sidewall surface 32 and the inner sidewall surface 30. The openings 42a can be any suitable shape and size to permit compression of the implant sleeve 10 in any suitable manner, such as along or proximate to the longitudinal axis A, and result in expansion of the first mesh portion 34 and the second mesh portion 36 outward and away from the longitudinal axis A, as described further herein. For example and as illustrated in FIGS. 1-3, the openings 42a can be provided in the form of a lattice structure with generally uniform and adjacent diamond-shaped openings of any suitable size, such as from about 0.25 mm to about 5.0 mm, such as about 1.0 mm. With additional reference to FIG. 4, the first mesh portion 34 and the second mesh portion 36 can each define openings 42b, which are generally spaced apart slots extending proximally to distally. For example and as illustrated, the slots may define a diamond shape. The openings 42b can be spaced-apart at any suitable distance, such as from about 0.10 mm to about 1.0 mm, such as about 0.5 mm, and can be of any suitable size, such as from about 0.25 mm to about 5.0 mm, such as about 1.0 mm or about 2.0 mm.

The first and second mesh portions 34 and 36 can also be provided with openings 42 of any other suitable size and shape, such as circular, hexagonal, octagonal, parallelogram, or rhombus shaped openings. The shape can be selected depending on the degree of retention force or grip desired between the implant sleeve 10 and surrounding bone. For example, upon compression of the implant sleeve 10 (as described herein), diamond shaped openings will have sharper edges to more securely engage surrounding bone as compared to, for example, circular openings. Hexagonal and octagonal shaped openings will often provide greater retention force than circular openings, but less than diamond shaped openings.

The intermediate sidewall portion 38 does not define or include openings therein, and cannot be compressed or expanded by force typically applied by hand in the operating room. The intermediate sidewall portion 38 can be located equidistant between the annular flange 18 and the distal sidewall portion 40 as illustrated. The intermediate sidewall portion 38 can also be at any other suitable location between the annular flange 18 and the distal sidewall portion 40, which would result in a change in relative length of the first mesh portion 34 with respect to the second mesh portion 36. The annular sidewall 20 may include multiple intermediate sidewall portions 38 spaced apart along the annular sidewall 20 with mesh portions similar to the first mesh portion 34 and the second mesh portion 36 therebetween. The intermediate sidewall portion 38 is optional. If the intermediate sidewall portion 38 is not included, then the first mesh portion 34 and the second mesh portion 36 can be combined into a single mesh portion that extends from the annular flange 18 to the distal sidewall portion 40 of the annular sidewall 20.

The distal sidewall portion 40 of the annular sidewall 20 is at the distal end 16 of the implant sleeve 10. The distal sidewall portion 40 does not define or include openings 42 therein, and is not compressible or expandable with a force typically applied by hand or with instruments in the operating room. As illustrated, the distal sidewall portion 40 does not extend beyond an outer diameter of the outer sidewall surface 32 and is thus flush with the outer sidewall surface 32. The distal sidewall portion 40 can include a flange similar to the annular flange 18 at the proximal end 14, which extends beyond an outer diameter of at least a portion of the second mesh portion 36.

Figure 5A:
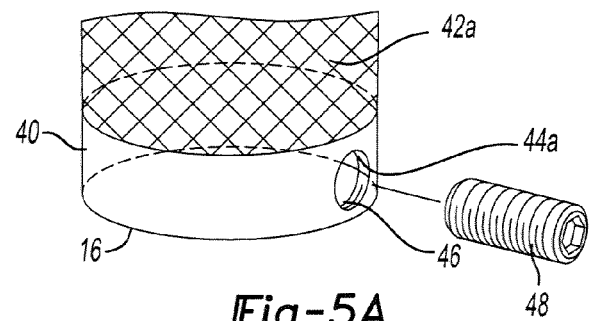
FIG. 5A illustrates the detail of area 5A of FIG. 2, and a threaded fastening device configured to cooperate with a threaded aperture of the implant sleeve.
Figure 5B:
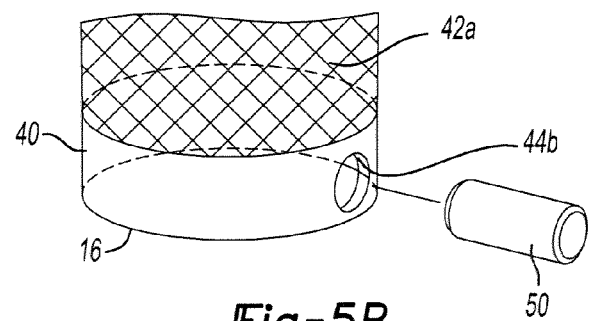
FIG. 5B is similar to FIG. 5A, but the aperture and fastening device are unthreaded.

The distal sidewall portion 40 may define an aperture 44a that extends entirely through the distal sidewall portion 40 between the inner sidewall surface 30 and the outer sidewall surface 32 of the annular sidewall 20. The aperture 44a can be any suitable shape or size to receive a fastener suitable to secure the implant sleeve 10 to a stem of an implant. As illustrated in FIGS. 2 and 5A, the aperture 44a is circular and includes internal threads 46, which are configured to cooperate with a threaded fastener 48. As illustrated in FIG. 5B, the aperture 44b can be unthreaded to receive unthreaded fastener pin 50.

Implant sleeve 10 can be manufactured in any suitable manner using any suitable manufacturing device and/or technique, such as wire electrical discharge machining, laser cutting, furnace brazing, fusion bonding, EOS laser sintering, and rapid metal prototyping. For example, the implant sleeve 10 can be formed from a solid metal tube using wire electrical discharge machining to cut completely through the annular sidewall 20 to form the openings 42a and 42b therein, as well as the apertures 44a and 44b. Also, lattice material defining the openings 42 can be connected, such as by welding, to the annular flange 18 and the distal sidewall portion 40.

FIGS. 6 and 7 illustrate the implant sleeve 10 mounted to a femoral implant 110 at a stem 112 of the implant 110. The stem 112 is inserted into the interior area 12 of the femoral implant 110 such that a distal tip 114 of the stem 112 extends beyond the distal end 16 of the implant sleeve 10. If the implant sleeve 10 is provided with aperture 44a, then threaded fastener 48 can be threaded into and through the aperture 44a to engage a receptacle 116 (FIG. 7) in the stem 112, thereby securing the implant sleeve 10 to the stem 112. The receptacle 116 may be threaded to further secure the threaded fastener 48 therein. If the implant sleeve 10 is provided with unthreaded aperture 44b, the fastener pin 50 can be inserted through the aperture 44b to engage the receptacle 116 and secure the implant sleeve 10 to the stem 112. The implant sleeve 10 is mounted to a distal portion of the stem 112, and does not extend to a neck 118 of the femoral implant 110. Generally, the sleeve 10 coincides with a portion of the stem 112 to assist in securing the stem 112 in a femur 210.

Figure 14:
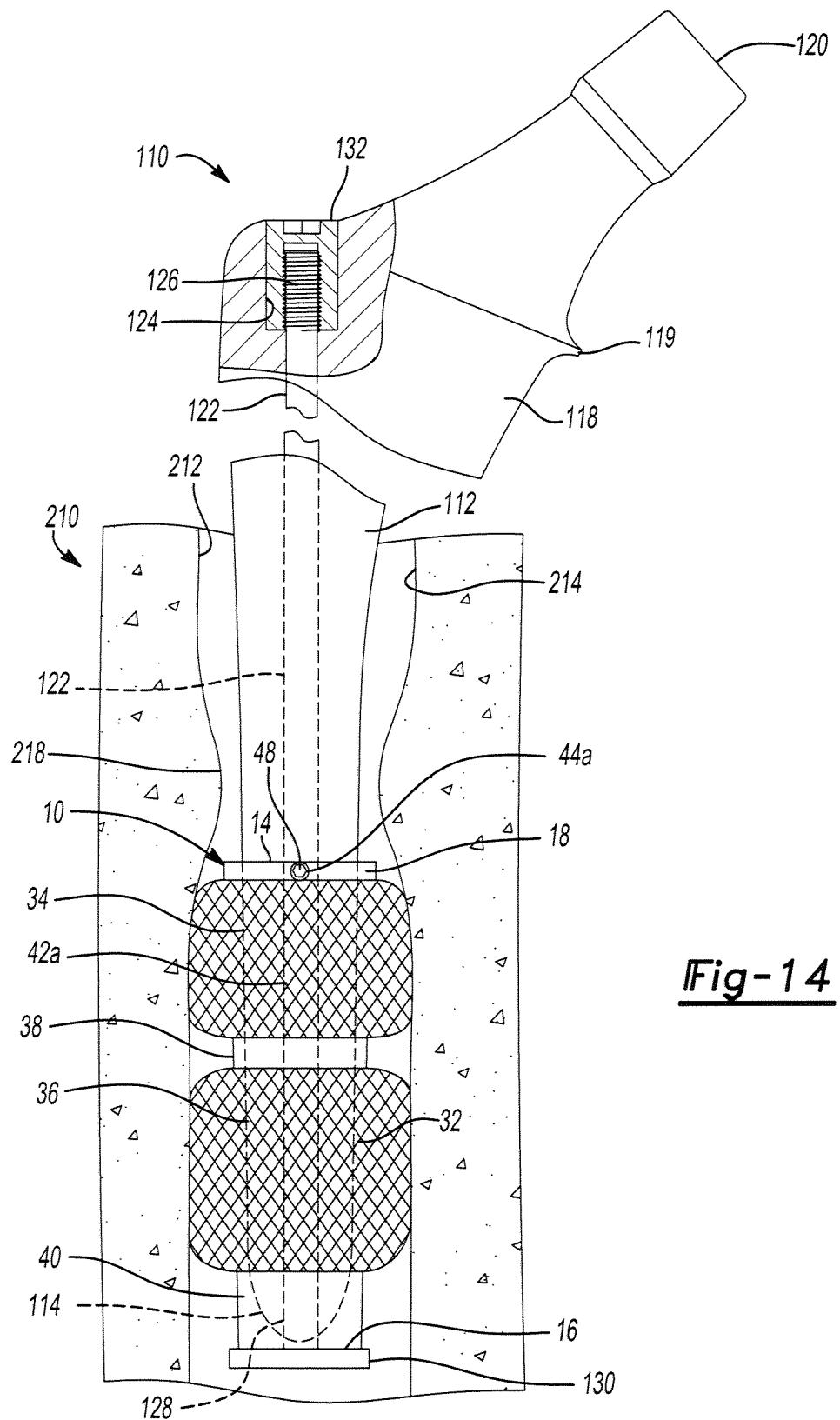
FIG. 14 is a cross-sectional view of the femur, the femoral implant and implant sleeve of FIG. 13 are implanted in the intramedullary canal distal to the isthmus.

With additional reference to FIG. 8, the femoral implant 110 with the implant sleeve 10 mounted thereto is implanted in femur 210. Prior to implantation, an intramedullary canal 212 of the femur 210 is prepared for receipt of the femoral implant 110 in any suitable manner, such as with a broach or reamer. The femoral implant 110 with the implant sleeve 10 mounted thereto is seated within the intramedullary canal 212 such that a collar 119 rests on a proximal surface of the femur 210. With reference to FIG. 8, the implant stem 112 can be positioned proximal to the isthmus 218 of the femur 210. Depending on the length of the stem 112 and the length of the femur 210, and as further described herein, the implant sleeve 10 can also be positioned at the isthmus 218 (FIG. 12) or distal to the isthmus 218 (FIG. 14).

With additional reference to FIG. 9, a compression tool is generally illustrated at reference numeral 310. The compression tool 310 is configured for use in applying compressive force to the implant sleeve 10 to compress the implant sleeve 10 along the longitudinal axis A. The compression tool 310 is rigid and includes a handle 312. The handle 312 includes a base 314, from which extends a shaft 316. The shaft 316 is semi-circular to permit the shaft 316 to extend around and past the neck 118 and head 120 of the femoral implant 110 and contact the annular flange 18 of the implant sleeve 10. The shaft 316 has a distal end 318. The distal end 318 has a shape and width that is complementary to the proximal flange surface 22 of the annular flange 18 to facilitate contact between the distal end 318 and the proximal flange surface 22.

Figure 10:
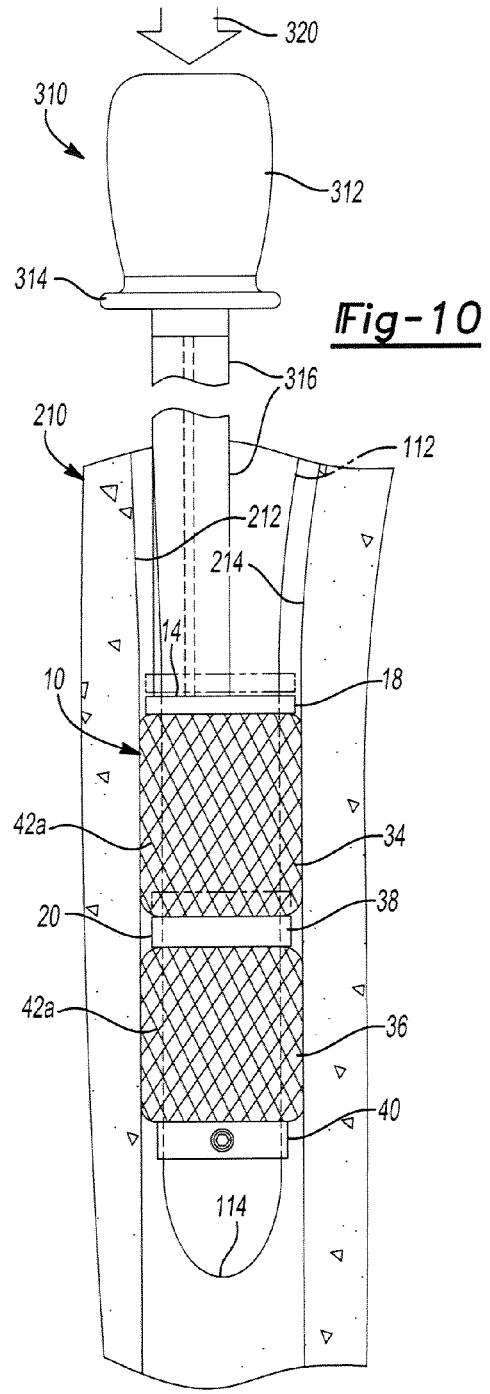
FIG. 10 illustrates the implant sleeve compressed with the compression tool to move the implant sleeve to an expanded position.

With additional reference to FIGS. 10 and 11, compression of the implant sleeve 10 with the compression tool 310 when positioned proximal to the isthmus 218 will be described. The shaft 316 of the compression tool 310 is inserted into the intramedullary canal 212 so that the shaft 316 makes initial contact with the annular flange 18. The compression tool 310 is then driven further into the intramedullary canal 212 and against the annular flange 18 to compress the flange 18 along the longitudinal axis A so that the proximal end 14 and the distal end 16 are moved closer together. The compression tool 310 may be driven into the intramedullary canal 212 in any suitable manner, such as by hand or with an impactor (e.g. hammer) generally in the direction of arrow 320. The compression tool 310 is one example of a device that can be used to compress the implant sleeve 10. Any other suitable device or method for compressing the implant sleeve 10 can be used.

During compression of the implant sleeve 10, the first mesh portion 34 and the second mesh portion 36 compress and expand generally evenly outward to contact and conform to the shape of interior walls 214 of the intramedullary canal 212. As a result of the contact between the first and second mesh portions 34 and 36 and the interior walls 214, the implant sleeve 10 is anchored and centered in the intramedullary canal 212—thereby anchoring and centering the femoral implant 110 in the intramedullary canal 212, as illustrated in FIG. 11. During compression of the implant sleeve 10, the annular flange 18, the intermediate sidewall portion 38, and the distal sidewall portion 40, do not substantially compress or expand relative to the mesh portions 34, 36. Thus, the stem 112 remains centered in the implant sleeve 10 due to contact between the stem 112 and each of the inner flange surface 28 of the annular flange 18, the inner sidewall surface 30 of the intermediate sidewall portion 38, and the distal sidewall portion 40.

Figure 11:
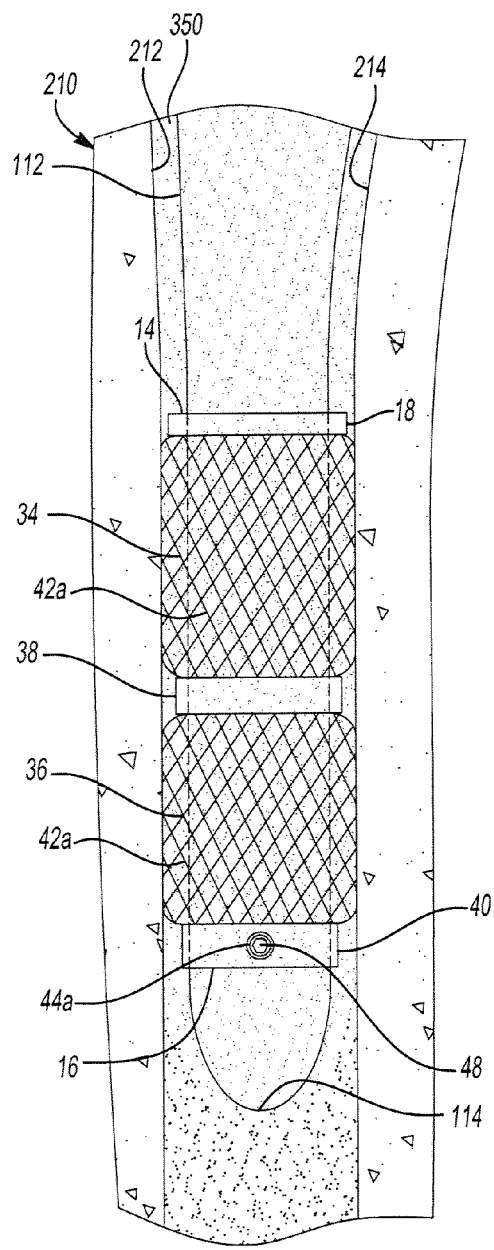
FIG. 11 illustrates the femoral implant with the implant sleeve mounted thereto secured in the intramedullary canal with bone cement.

With continued reference to FIG. 11, the femoral implant 110 and the implant sleeve 10 can be further anchored in the intramedullary canal 212 with bone cement 350. The bone cement 350 is introduced into the intramedullary canal such that it surrounds the femoral implant 110 and passes through the openings 42a of the expanded first and second mesh portions 34 and 36 of the implant sleeve 10 to form a cement mantle around the femoral implant 110. The first mesh portion 34 and the second mesh portion 36 serve as structural reinforcements for the bone cement mantle, which enhances the strength and longevity of the cement mantle and fixation of both the femoral implant 110 and the implant sleeve 10 in the intramedullary canal 212.

The bone cement 350 can be any suitable bone cement such as Cobalt™ Bone Cement sold by Biomet of Warsaw, Ind., or other bone cements including those sold under the trademarks Palacos®, or Simplex®. The bone cement 350 can include various materials to facilitate bacterial resistance, such as any suitable antibiotic, including Gentamicin.

Figure 12:
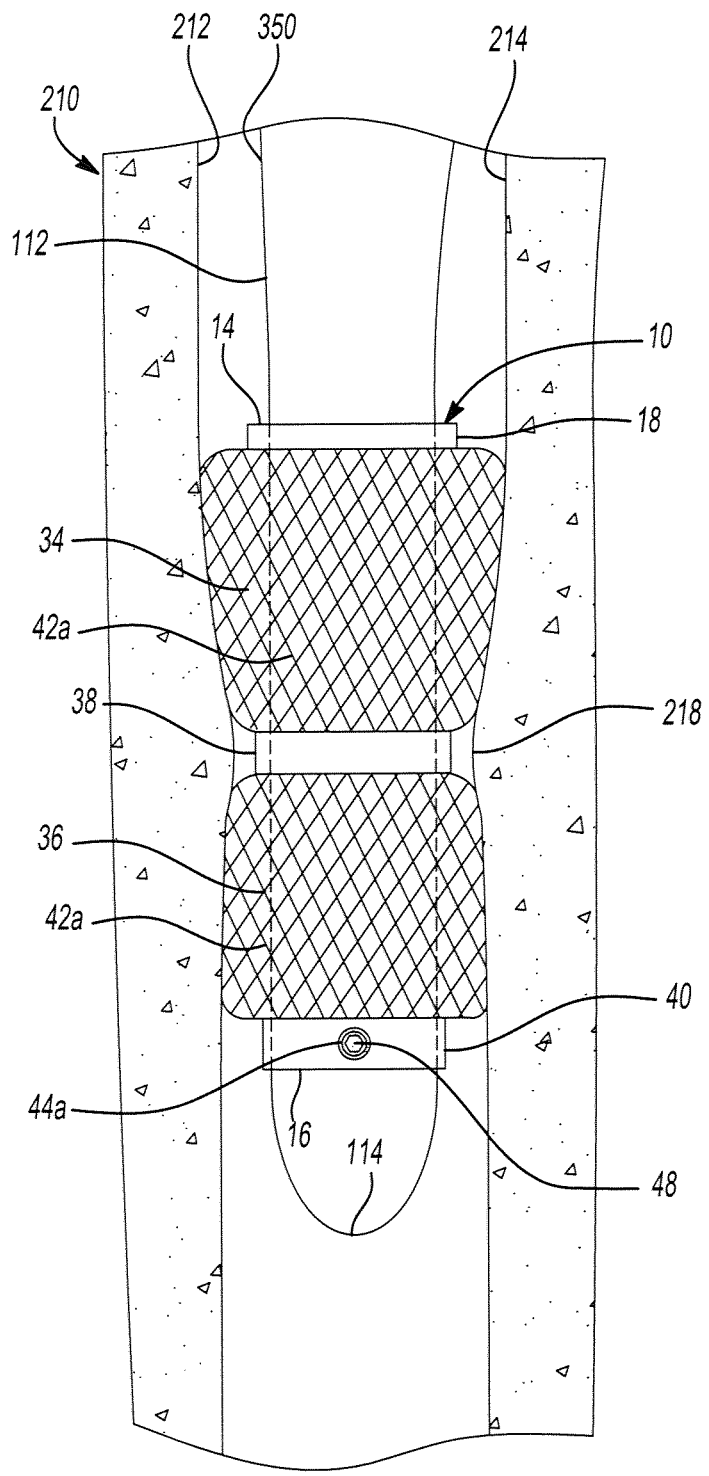
FIG. 12 illustrates the femoral implant with the implant sleeve mounted thereto secured at the isthmus of the intramedullary canal without bone cement.

With additional reference to FIG. 12, the implant sleeve 10 can be implanted at the isthmus 218 of the femur 210. Using the compression tool 310, the implant sleeve 10 can be compressed so that the first mesh portion 34 and the second mesh portion 36 compress and expand to engage and conform to the shape of the interior walls 214 of the intramedullary canal 212 at the isthmus 218. Because the isthmus 218 is the most narrow portion of the intramedullary canal 212, compression of the sleeve 10 at the isthmus 218 can result in more secure engagement with the interior walls 214, which can make bone cement unnecessary. FIG. 12 illustrates the implant sleeve 10 implanted without bone cement.

Figure 13:
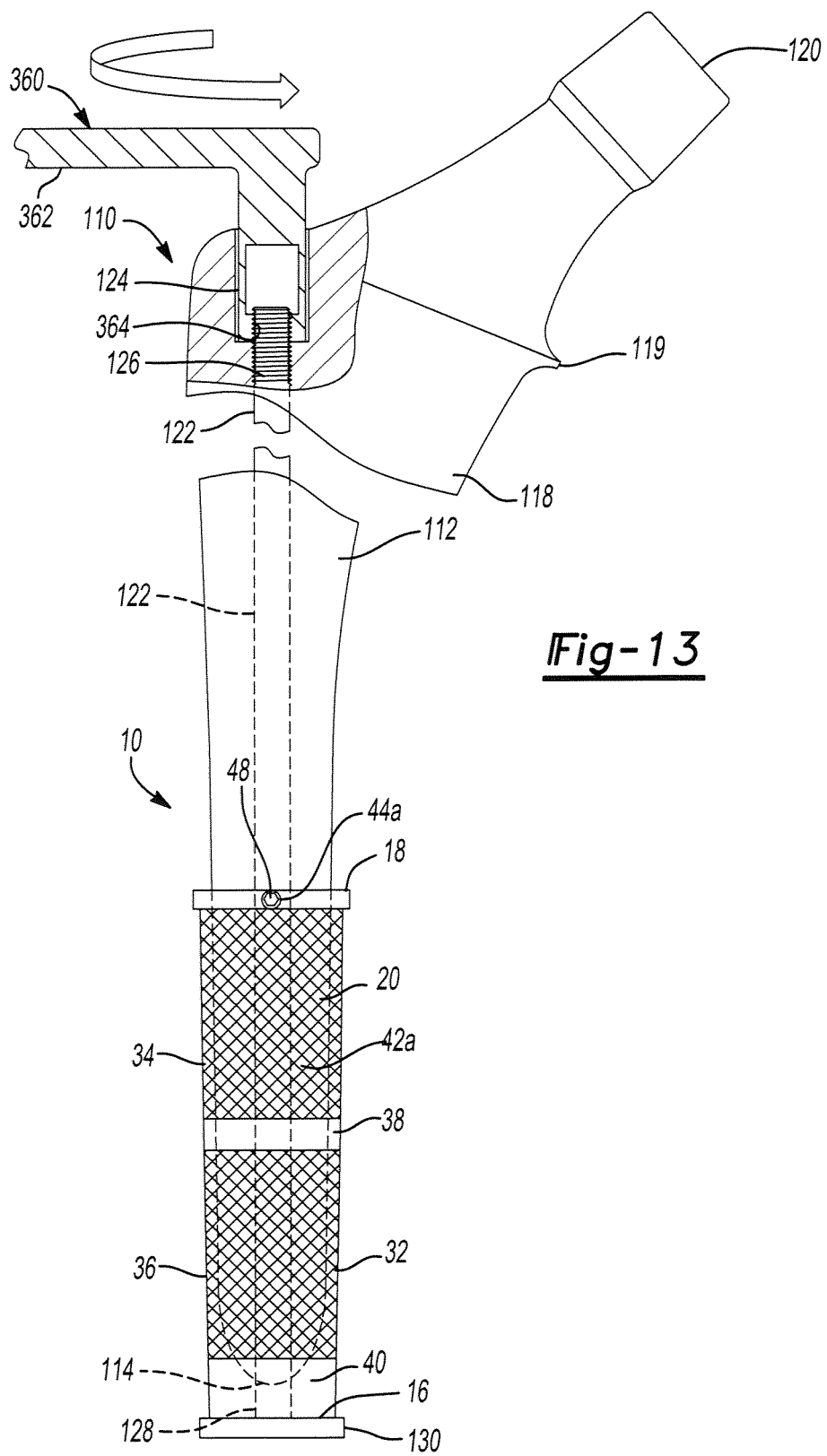
FIG. 13 is a side view of the implant sleeve mounted on another femoral implant, the implant sleeve configured to be compressed from a distal end thereof by a retraction rod of the implant.

With reference to FIGS. 13 and 14, the implant sleeve 10 can be implanted in the intramedullary canal 212 distal to (or beyond) the isthmus 218. To implant the sleeve 10 distal to the isthmus 218, the femoral implant 110 includes a retraction rod 122, which extends from a receptacle 124 in the neck portion 118, through the stem 112, and out from the distal tip 114 of the femoral implant 110. The retraction rod 122 also extends beyond the distal end 16 of the sleeve 10, which is also positioned to extend beyond the distal tip 114. The retraction rod 122 includes a proximal threaded end 126, which is seated within the receptacle 124, and a distal end 128, which is mounted to a base 130. The base 130 is connected to the distal end 16 of the implant sleeve 10. The annular flange 18 of the sleeve 10 includes the aperture 44a, which receives the fastener 48 to rigidly mount the sleeve 10 to the stem 112 at the annular flange 18.

The receptacle 124 is configured to receive a suitable tool for cooperating with the proximal threaded end 126, such as a ratchet 360 (FIG. 13). The ratchet 360 includes a handle 362 and internal threads 364. Cooperation between the threads 364 and the proximal threaded end 126, and rotation of the ratchet 360 relative to the compression rod 122 (FIG. 13), draws the compression rod 122 further into the receptacle 124 and pushes the base 124 against the distal end 16 of the sleeve 10, which compresses and expands the sleeve 10 because the annular flange 18 is fixed to the stem 112 (FIG. 14).

Thus, the implant sleeve 10 can be compressed from the distal end 16 with the retraction rod 122 to avoid having to pass compression tools, such as the tool 310, beyond the isthmus 218. The retraction rod 122 can be secured in the retracted position of FIG. 14 with, for example, a cap 132 threaded onto the proximal threaded end 126.

Figure 17:
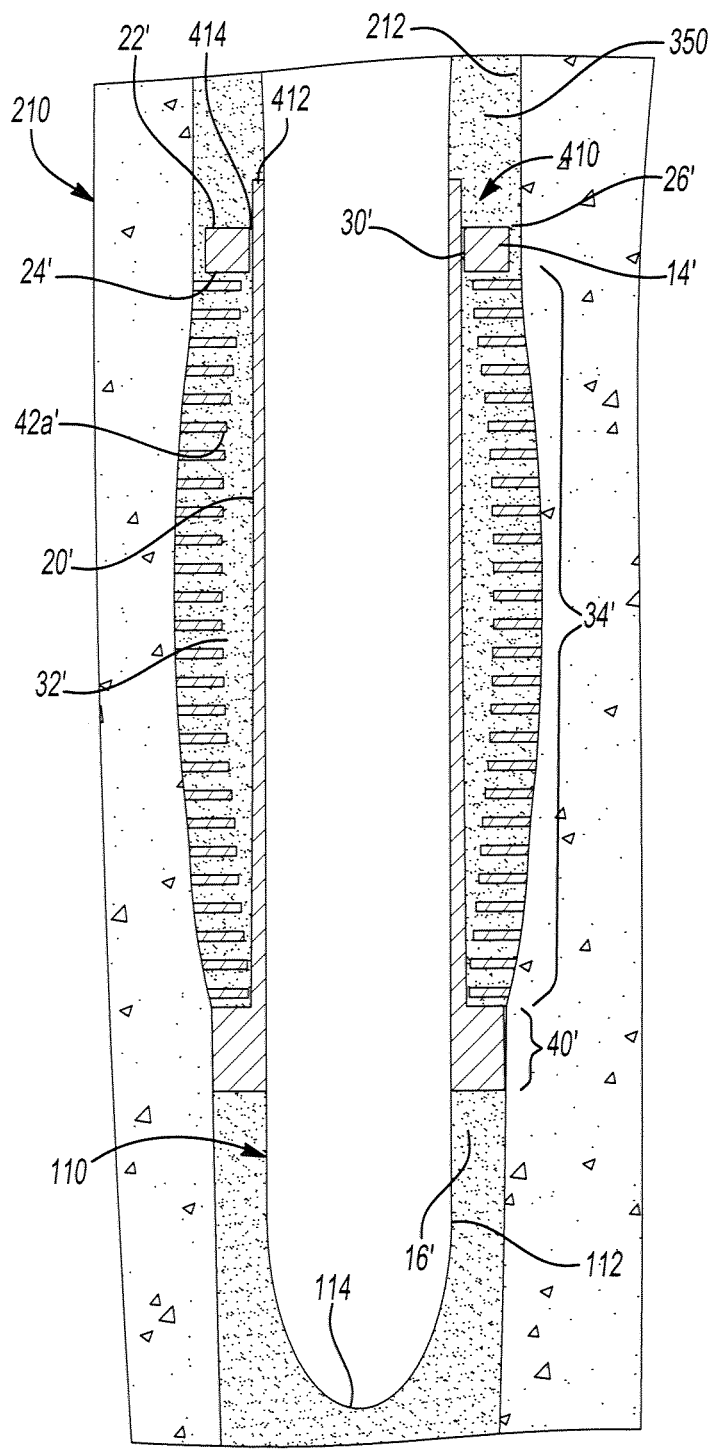
FIG. 17 is a cross-sectional view of the implant sleeve of FIG. 15 mounted on a femoral implant stem and implanted in the femur.

With additional reference to FIGS. 15-17, an additional implant sleeve according to the present teachings is generally illustrated at reference number 410. The implant sleeve 410 includes numerous similarities with the implant sleeve 10. Therefore, features of the implant sleeve 410 that are similar to features of the implant sleeve 10 are designated with the same reference numbers, and the prime (') symbol. The description of the implant sleeve 10 also applies to the implant sleeve 410 with respect to the common features.

The implant sleeve 410 includes an inner annular sidewall 412 that is closer to the longitudinal axis A than the annular sidewall 20'. The inner annular sidewall 412 is generally solid and does not include openings extending there through. The annular sidewall 20' is connected to the distal sidewall portion 40', but not otherwise connected to the inner annular sidewall 412. The annular sidewall 20' includes mesh portion 34', which defines openings 42a' as illustrated. The openings 42a' extend entirely through the annular sidewall 20', thereby making the annular sidewall 20' compressible and expandable independent of the inner annular sidewall 412. The mesh portion 34' may alternatively define openings 42b' or any other openings of a suitable size and shape.

As illustrated in FIG. 17, the femoral implant 110 is inserted in the implant sleeve 410 such that the stem 112 abuts the inner annular sidewall 412. After the implant sleeve 410 is implanted in the intramedullary canal 212, the annular sidewall 20' is compressed along the longitudinal axis A, such as with the tool 310, to force the mesh portion 34' outward and into contact with the intramedullary canal 212. The inner annular sidewall 412 is not compressed, and remains in contact with the stem 112 to retain the stem 112 centered in the implant sleeve 410. Bone cement 350 can be subsequently introduced into the intramedullary canal 212 to form a cement mantle. The bone cement 350 may enter a gap 414 formed between the annular sidewall 20' and the inner annular sidewall 412 to enhance fixation of the implant sleeve 410 in the intramedullary canal.

The implant sleeve 410 can be manufactured in any suitable manner using any suitable manufacturing device and/or technique. For example, the implant sleeve 410 can be laser formed and/or cut from a solid metal tube. Using a laser, the openings 42a' can be cut in and through the annular sidewall 20' only, without cutting openings in the inner annular sidewall 412, such that the inner annular sidewall 412 remains solid. The annular sidewall 20' is cut and formed so that it is connected to the distal sidewall portion 40', but not otherwise connected to the inner annular sidewall 412. As a result, the annular sidewall 20' is configured to be compressed independently of the inner annular sidewall 412, such as is illustrated in FIG. 17. Also, the annular sidewall 20' with the openings 42a' formed therein in any suitable manner can be manufactured separate from the remainder of the implant sleeve 410 and mounted to the distal sidewall portion 40' in any suitable manner, such as by welding.

While the implant sleeve 10 and the implant sleeve 410 have been described herein for use with the stem 112 of femoral implant 110, the implant sleeves 10 and 110 can be used to center any implant having a stem at an implantation site, for example, a stem of a tibial tray or humeral prosthesis.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An implant sleeve operable to center an implant at an implantation site, the implant sleeve comprising:
   a first rigid end;
   a second rigid end;
   a shaped outer sidewall between the first rigid end and the second rigid end;
   a mesh portion of the outer sidewall that defines a plurality of openings in the outer sidewall; and
   an interior area encompassed by the outer sidewall and configured to receive a stem of the implant, a longitudinal axis of the implant sleeve extends along an axial center of the interior area;
   wherein in response to force applied to the implant sleeve along the longitudinal axis to compress the implant sleeve, the implant sleeve compresses and the mesh portion expands outward from the longitudinal axis.

2. The implant sleeve of claim 1, wherein the sleeve compresses and the mesh portion expands outward from the longitudinal axis in response to force applied to the implant sleeve along the longitudinal axis to one of the first end or the second end; and
   wherein the first rigid end and the second rigid end are non-flexible.

3. The implant sleeve of claim 1, wherein the outer sidewall is tapered from the first end to the second end, the first end is a proximal end and the second end is a distal end.

4. The implant sleeve of claim 1, wherein the outer sidewall includes an intermediate sidewall portion between the first end and the second end, the intermediate sidewall portion is substantially solid;
   wherein the mesh portion includes a first mesh portion between the intermediate sidewall portion and the first end, and a second mesh portion between the intermediate sidewall portion and the second end;
   wherein in response to force applied to the proximal end parallel to the longitudinal axis, the intermediate sidewall portion moves along the longitudinal axis and remains at a generally constant distance from the longitudinal axis; and
   wherein the first end is a proximal end and the second end is a distal end of the implant sleeve.

5. The implant sleeve of claim 1, wherein the openings include slots extending in a distal to proximal direction.

6. The implant sleeve of claim 1, wherein the outer sidewall includes a distal sidewall portion at the second end that defines a threaded aperture configured to receive a threaded fastening device.

7. The implant sleeve of claim 1, wherein the implant sleeve is formed entirely of a metal.

8. The implant sleeve of claim 1, wherein the a stem of the implant is a stem of a femoral implant that includes a compression rod configured to compress the implant sleeve from the second end, which is a distal end proximate to a distal tip of the implant.

9. The implant sleeve of claim 1, further comprising a solid interior sidewall that is between the outer sidewall and the longitudinal axis, the outer sidewall is compressible and expandable independent of the interior sidewall.

10. An implant sleeve operable to center an implant at an implantation site, the implant sleeve comprising:
   a rigid first end portion at a first end of the implant sleeve;
   an annular sidewall extending from the rigid first end portion to a second end of the implant sleeve, the annular sidewall defining an interior area of the implant sleeve that is configured to receive a stem of the implant;
   a rigid second end portion at the second end of the implant sleeve;
   an aperture defined by one of the rigid first end portion and the rigid second end portion that is configured to receive a fastener there through to secure the implant sleeve to the stem; and
   a mesh portion forming a portion of the annular sidewall between the rigid first end portion and the rigid second end portion, the mesh portion expands outward from a longitudinal axis of the interior area in response to a compression force applied along the longitudinal axis to one of the rigid first end portion or the rigid second end portion.

11. The implant sleeve of claim 10, wherein the mesh portion expands outward from the longitudinal axis in response to a compression force applied along the longitudinal axis to a rigid annular flange at the rigid first end portion.

12. The implant sleeve of claim 10, wherein the interior area is tapered from the rigid first end portion to the rigid second end portion.

13. The implant sleeve of claim 10, wherein the rigid first end portion and the rigid second end portion remain at a constant distance from the longitudinal axis as the implant sleeve is compressed in response to the compression force.

14. The implant sleeve of claim 10, wherein the implant sleeve is formed entirely of a metal.

15. The implant sleeve of claim 10, wherein the implantation site includes an intramedullary canal of a femur and the implant includes a femoral implant configured to be secured in the intramedullary canal.

16. An implant sleeve operable to center an implant at an implantation site, the implant sleeve comprising:
   a rigid proximal end defining a first diameter;
   a rigid distal end defining a second diameter that is smaller than the first diameter, the rigid proximal end and the rigid distal end are aligned along a longitudinal axis of the implant sleeve;
   an annular sidewall extending from the rigid proximal end to the rigid distal end, the annular sidewall is generally cylindrical and is tapered along its length such that the annular sidewall has a greater diameter at the rigid proximal end than at the rigid distal end;
   an interior area encompassed by the annular sidewall and configured to receive a stem of the implant, a longitudinal axis of the implant sleeve extends along an axial center of the interior area;
   an aperture defined by one of the rigid proximal end and the rigid distal end that is configured to receive a fastener therethrough to secure the implant sleeve to the stem; and
   a mesh portion forming a portion of the annular sidewall between the rigid proximal end and the rigid distal end, the mesh portion expands outward from the longitudinal axis of the interior area in response to a compression force applied along the longitudinal axis to one of the rigid proximal end or the rigid distal end.

17. The implant sleeve of claim 16, wherein the rigid proximal end includes a proximal flange and the rigid distal end includes a distal flange.

18. The implant sleeve of claim 16, wherein the interior area is tapered inward from the rigid proximal end to the rigid distal end.

19. The implant sleeve of claim 16, wherein each of the rigid proximal end and the rigid distal end are non-flexible.

20. The implant sleeve of claim 16, wherein the implant sleeve is formed entirely of a metal.

* * * * *